US010815245B2

(12) United States Patent
Morvan et al.

(10) Patent No.: US 10,815,245 B2
(45) Date of Patent: Oct. 27, 2020

(54) PRODUCTION OF XYLENE DERIVATIVES

(71) Applicants: RHODIA OPERATIONS, Paris (FR); CENTRE NATIONAL DE LA RECHERCHE SCIENTIFIQUE, Paris (FR)

(72) Inventors: Didier Morvan, Mornant (FR); Olivier Back, Lyons (FR); Raphaël Wischert, Shanghai (CN); Eric Muller, Lyons (FR)

(73) Assignees: RHODIA OPERATIONS, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 16/060,510

(22) PCT Filed: Dec. 8, 2016

(86) PCT No.: PCT/CN2016/108997
§ 371 (c)(1),
(2) Date: Jun. 8, 2018

(87) PCT Pub. No.: WO2017/097220
PCT Pub. Date: Jun. 15, 2017

(65) Prior Publication Data
US 2018/0370984 A1 Dec. 27, 2018

(30) Foreign Application Priority Data
Dec. 9, 2015 (WO) ................ PCT/CN2015/096821

(51) Int. Cl.
*C07D 493/08* (2006.01)
*C07C 209/48* (2006.01)
*C07C 211/27* (2006.01)
*C07D 317/30* (2006.01)
*C07C 209/50* (2006.01)
*C07B 41/08* (2006.01)
*C07B 43/04* (2006.01)
*C07C 63/15* (2006.01)

(52) U.S. Cl.
CPC .......... *C07D 493/08* (2013.01); *C07C 209/48* (2013.01); *C07C 209/50* (2013.01); *C07C 211/27* (2013.01); *C07D 317/30* (2013.01); *C07B 41/08* (2013.01); *C07B 43/04* (2013.01); *C07C 63/15* (2013.01)

(58) Field of Classification Search
CPC .................................................. C07D 493/08
USPC ....................................................... 549/463
See application file for complete search history.

(56) References Cited

U.S. PATENT DOCUMENTS

| 2,405,267 | A | 8/1946 | Nudenberg |
| 4,723,986 | A | 2/1988 | Teach |
| 9,024,072 | B2 | 5/2015 | Molitor et al. |
| 2006/0040990 | A1 | 2/2006 | Klar et al. |

FOREIGN PATENT DOCUMENTS

| CN | 102574772 A | 7/2012 |
| WO | 00/47584 A2 | 8/2000 |
| WO | 2010151346 A1 | 12/2010 |
| WO | 2013048248 A1 | 4/2013 |
| WO | 2014065657 A1 | 5/2014 |
| WO | 2014197195 A2 | 12/2014 |

OTHER PUBLICATIONS

Cheng et. al.; "Chemistry of Furan Conversion into Aromatics and Olefins over HZSM-5: A Model Biomass Conversion Reaction"; ACS Catalysis 2011, vol. 1, pp. 611-628.
Cheng et. al.; "Production of targeted aromatics by using Diels-Alder classes of reactions with furans and olefins over ZSM-5"; Green Chemistry, 2012, vol. 14, pp. 3114-3125.
Wang et al.; Selective Production of Aromatics from Alkylfurans over Solid Acid Catalysts; ChemCatChem 2013, vol. 5, pp. 2044-2050.
Wu et al.; Raney Ni/KBH4: an efficient and mild system for the reduction of nitriles to amines; General Papers, ARKIVOC 2008 (xii), pp. 95-102.
Ryu et. al.; "Chemisty on Isoindoles. Novel Synthesis of Various Functionalized Isoindoles from 2,3-Dicyanobenzaldehydde"; Bulletin of the Chemical Society of Japan, 1990, vol. 63, No. 4, pp. 1160-1167.
Anderson E. et al., "Intramolecular Nucleophilic Assistance in Reactions of Acetals", Journal of the Chemical Society, Perkin Transactions 2: Physical Organic Chemi, Royal Society of Chemistry, GB, Jan. 1, 1972, pp. 515-522.
Kimberly J. Rutan et al., "On the Preparation of Aryl Nitriles Using Tosyl Cyanide", Journal of Organic Chemistry, vol. 60, No. 9, May 1, 1995, pp. 2948-2950.
Alexander S. Kiselyov et al:, "Efficient hydrolysis of dithioacetals by the N-fluoro-2, 4, 6-trimethylpyridinium triflate-water system", Tetrahedron, vol. 49, No. 11, Jan. 1, 1993, pp. 2151-2158.
Lindsey J. S. et al., "Rothemund and Adler-Longo Reactions Revisited. Synthesis of Tetraphenylporphyrins under Equilibrium Conditions", Journal of Organic Chemistry, American Chemical Society, US, vol. 52, No. 5, Mar. 6, 1987, pp. 827-836.
Ali Pourjavadi et al., "Microwave-assisted Rapid Ketalization/ Acetalization of Aromatic Aldehydes and Ketones in Aqueous Media", Journal of Chemical Research—Synopses, No. 9, Jan. 1, 1999, pp. 562-563.
Stephen Hanessian et al., "Proximity-Assisted Cycloaddition ReactionsFacile Lewis Acid-Mediated Synthesis of Diversely Functionalized Bicyclic Tetrazoles", Organic Letters, vol. 10, No. 7, Apr. 1, 2008, pp. 1381-1384.
Balachari D. et al., "Efficient synthesis of 5-aryl-2-vinylfurans by palladium catalyzed cross-coupling strategies", Tetrahedron Let, Elsevier, Amsterdam, NL, vol. 40, No. 26, Jun. 25, 1999, pp. 4769-4773.

(Continued)

Primary Examiner — Taofiq A Solola

(57) ABSTRACT

The present invention relates to the production of xylene derivatives from furfural and its derivatives. The invention describes new routes for converting furfural and its derivatives into xylene derivatives including novel intermediates.

15 Claims, No Drawings

(56) References Cited

OTHER PUBLICATIONS

Thomas Ullrich et al., "Scope and Applicability of an Expedient Synthesis Leading to Polysubstituted 3- (Carboxyphenyl)pyrroles", Synthetic Communications, vol. 37, No. 7, Apr. 1, 2007, pp. 1109-1119.
Tomonori Kawabata et al., " Highly Efficient Deprotection of Acetals by Titanium Cation-exchanged Montmorillonite as a Strong Solid Acid Catalyst", Chemistry Letters, vol. 32, No. 7, Jul. 1, 2003, pp. 648-649.
Stephan Herre et al., "Synthesis of Photoswitchable Hemithioindigo-Based [omega]-Amino Acids and Application in Boc-Based Peptide Assembly", Synthesis, No. 19, Jan. 1, 2005, pp. 3297-3300.
Hanif Aslam M. et al., "The separation of polar and steric effects. part 14. Kinetics of the reactions of benzoic acid and of ortho-substituted benzoic acids with diazodiphenylmethane in various alcohols", Journal of the Chemical Society, Perkin Transactions 2: Physical Organic Chemi, 1981, pp. 500-508.
Soren Christian Schou, "Fast and efficient synthesis of 14 C labelled benzonitriles and their corresponding acids", Journal of Labelled Compounds and Radiopharmaceuticals, vol. 52, No. 5, May 15, 2009, pp. 173-176.
Database Registry [online] Chemical Abstracts Service, Columbus, Ohio, US, Apr. 9, 2010.
Louis A.. Carpino, "New Methods of Introducing the Carbo-t-butoxy Amino-Protecting Group. Preparation and Use of t-Butyl Cyanoformate and t-Butyl Iminodicarboxylate 1", Journal of Organic Chemistry, vol. 29, No. 10, Oct. 1, 1964, pp. 2820-2824.
Ikoma et al., "Synthesis and domino metathesis of functionalized 7-oxanorbornene analogs toward cis-fused heterocycles", Tetrahedron, Elsevier Science Publishers, Amsterdam, NL, vol. 64, No. 12, Jan. 19, 2008, pp. 2740-2749.
Greene W. et al., "Protection for the Carbonyl Group", Protective Groups in Organic Synthesis,Third dition, 1999, John Wiley & Sons, Inc., pp. 293-368.

PRODUCTION OF XYLENE DERIVATIVES

This application is a U.S. national phase entry under 35 U.S.C. § 371 of International Application No. PCT/CN2016/108997, filed on Dec. 8, 2016, which claims priority to CN Application No. PCT/CN2015/096821, filed on Dec. 9, 2015. The entire contents of these applications are explicitly incorporated herein by this reference.

The present invention relates to the production of xylene derivatives and in particular ortho-xylenediamine, meta-xylenediamine and 1,2,3-tri(aminomethyl)benzene from furfural and its derivatives. The invention describes new routes for converting furfural and its derivatives into xylene derivatives including novel intermediates.

In recent times, a tendency has grown to obtain a variety of chemicals from renewable sources. In this context, there has been a tendency to create chemicals from biomass carbohydrates, such as cellulose, starch, hemicellulose, sugars and the like. Under dehydration conditions, these carbohydrates can be converted into a number of interesting chemicals, including furfural, hydroxymethyl furfural and derivatives thereof. There is an interest to use these chemicals for the production of value-added chemical compounds. Examples of such value-added chemical compounds include orthophthalic acid (commonly named phthalic acid), terephthalic acid, isophthalic acid, trimellitic acid, hemimellitic acid, pyromellitic acid and other benzene derivatives that contain two or more carboxylic moiety substituents.

One approach to transfer furane, furfural and their derivatives into chemically more valuable six-membered ring aromatic compounds is the Diels-Alder reaction between the furane ring system and ethylene or ethylene derivatives.

The Diels-Alder reaction with furane derivatives is known. The Diels-Alder reaction of furane and ethylene to 3,6-epoxycyclohexane has been described in U.S. Pat. No. 2,405,267:

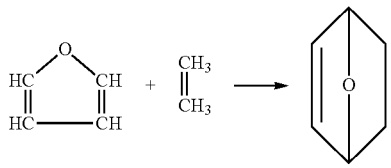

WO 2010/151346 describes the conversion of 2,5-dimethylfurane to para-xylene.

A process for the preparation of a substituted benzene derivative by reacting a furfuryl ether with an ethylene derivative is described in WO 2013/048248.

WO 2014/065657 broadly claims a process for the preparation of benzene derivatives by reacting a furane derivative with ethylene. The furane derivative may bear at 2 and 5 position a variety of substituents including alkyl, aralkyl, —CHO, —CH$_2$OR$^3$, —CH(OR$^4$)(OR$^5$) and —COOR$^6$. However, this document provides examples only with 2,5-dimethylfurane, 2-methylfurane, 2,5-furane dicarboxylic acid and the dimethylester of 2,5-furane dicarboxylic acid. In particular, there is no example wherein furfural is converted into a benzene derivative.

Yu-Ting Cheng, et al. in Green Chem., 2012, 14, 3314-3325 provide an overview over the production of targeted aromatics by using Diels-Alder classes of reactions with furanes and olefins. The authors found that while furane, methylfurane and dimethylfurane react smoothly with olefins, the first step for furfural conversion is decarbonylation to form furane and CO. The produced furane then enters the known furane conversion reaction:

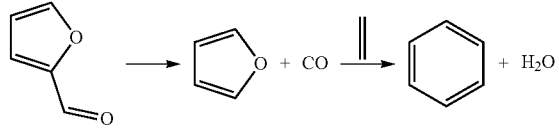

These difficulties in reacting furfural with olefins are confirmed in WO 2014/197195. Although the authors of this document conducted screening experiments, testing range of various solvents, catalysts, reaction temperatures, pressures and times, and 5-hydroxy-2-furfural concentrations, they failed to identify a system in which 4-hydroxymethylbenzaldehyde formed (example 4.3). The authors suggest solving this problem by air oxidation of 5-hydroxymethyl-2-furfural to generate the corresponding 5-hydroxymethyl-2-furoic acid or other oxidized derivative, which has been shown to work well in the Diels-Alder reaction with olefins.

Both, decarbonylation of furfural to furane as well as oxidation of furfural to furoic acid has the disadvantage that the aldehyde substituent at the furane ring is lost. As a consequence thereof, the aldehyde substituent is no longer present in the obtained Diels-Alder adduct which makes it more difficult to obtain benzaldehyde derivatives from furane derivatives and in particular furfural. However, benzaldehyde derivatives are desirable as valuable intermediates in the preparation of other important chemical compounds, such as meta-xylenediamine, ortho-xylenediamine and 1,2,3-tri(aminomethyl)benzene.

In order to solve the above problems, the present inventors conducted various experiments in an effort to react furfural with ethylene derivatives. As expected from the prior art, no reaction between furfural and acrylonitrile was observed even under varying conditions with respect to catalyst, molar ratio of the reactants, temperature and reaction time. The inventors then converted the aldehyde substituent of furfural into its diethyl-ketal. Ketals are known derivatives of aldehydes from which the desired aldehyde can easily be obtained by removing the alcohol. However, when reacting the diethyl-ketal of furfural with acrylonitrile, only traces of the Diels-Alder adduct, the oxanorbornene were observed. Upon further investigations, the inventors then found that cyclic ketals of furfural surprisingly react with acrylonitrile thereby forming the desired Diels-Alder adduct. In further reaction stages, the cyclic ketal can be converted back into the desired aldehyde substituent which, if required, can be further reacted to other substituents. This finding is particularly surprising when considering that the dialkyl-ketal derivative of furfural does not form a Diels-Alder adduct with ethylene derivatives.

During the investigations, the present inventors additionally found that cyclic ketals of furfural surprisingly react with only certain ethylene derivatives. It was, for example, found that cyclic ketals of furfural do not react with allyl amines and acryl amides. Only acrylonitrile and fumaronitrile smoothly reacted in the Diels-Alder condensation reaction.

The present invention therefore relates to a process for the preparation of a compound of Formula (I)

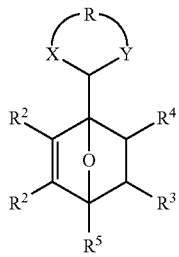

wherein

X and Y independently are optionally substituted heteroatoms;

R is a $C_{1-4}$ alkylene group which may optionally be substituted with one or more $R^1$.

$R^1$ is a linear, branched and/or cyclic, saturated or unsaturated hydrocarbon group which optionally bears one or more functional groups;

$R^2$ independently is H, alkyl, alkenyl or aryl;

$R^3$ and $R^4$ independently are H or —CN, provided that at least one of $R^3$ and $R^4$ is —CN;

$R^5$ is $R^2$, —CH$_2$OR$^2$, —CO$_2$R$^2$ or

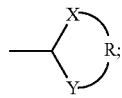

which comprises reacting a compound of the Formula (II)

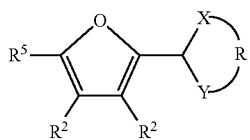

wherein X, Y, R, $R^2$ and $R^5$ are defined as above;
with a compound of the Formula (III) or (III')

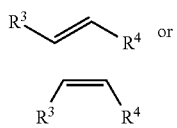

wherein $R^3$ and $R^4$ are defined as above.

The furane derivative of Formula (II) that is being used as starting material can be derived from a biomass resource. For example, the furane derivative can be derived from the dehydration of a carbohydrate. The carbohydrate is suitably selected from polysaccharides, oligosaccharides, disaccharides and monosaccharides. Suitable biomass sources as well as suitable methods for their conversion into furfural derivatives are known to the person skilled in the art. Alternatively, the furfural derivative can be a commercially available chemical product obtained by usual chemical reactions.

In the furfural derivative of Formula (II) the aldehyde residue of furfural is present as cyclic ketal. However, the present invention is not limited to furfural and its cyclic ketal derivative but also includes furane derivatives comprising heteroatoms other than O. Therefore, X and Y in the compound of Formula (II) are independently of each other optionally substituted heteroatoms, such as O, S and N. In this context, "optionally substituted" defines that the heteroatom may bear a substituent, if required. If the heteroatom cannot bear any further substituent, no substituent is present. For example, if the heteroatom is O or S, there is no substituent at the heteroatom. However, if the heteroatom is N, then X and Y may be —NH— or —N(substituent)-. This substituent has the same meaning as Thus, X and Y are preferably independently selected from —O—, —S—, —NH—, and —N(R$^1$)—, more preferably from —O— and —S—. Most preferably, X and Y are both O or both S.

In the furfural derivative of Formula (II), R is a $C_{1-4}$ alkylene group, preferably a $C_{2-4}$ alkylene group, more preferably, a $C_{2-3}$ alkylene group, most preferably a $C_2$ alkylene group. This alkylene group may optionally be substituted with one or more $R^1$ substituents. $R^1$ is a linear, branched and/or cyclic, saturated or unsaturated hydrocarbon group which optionally bears one or more functional groups. Such hydrocarbon groups include all chemical moieties comprising carbon atoms, preferably from 1 to 24 carbon atoms besides the required number of hydrogen atoms. Examples of linear, branched, and/or cyclic, saturated or unsaturated hydrocarbon groups are alkyl, alkenyl, alkynyl, aromatic groups, etc. The hydrocarbon group may optionally bear one or more functional groups which means that the hydrocarbon group may contain one or more heteroatoms, such as O, N and S, or functional groups, such as —CO— or —COO—. Furthermore, the hydrocarbon group may be substituted with functional groups, such as nitro, nitroso, sulfo, sulfonate, cyano, cyanato, thiocyanato, amino, hydroxyl, carboxyl, etc.

Representative examples of $R^1$ will now be explained in more detail, thereby also providing definitions of certain terms which are applicable throughout the present specification and in particular also for all other substituents, if not defined otherwise.

The term "alkyl" as used herein refers to a linear, branched, or cyclic saturated hydrocarbon group typically although not necessarily containing 1 to about 24 carbon atoms, preferably 1 to about 12 carbon atoms, or 1 to about 6 carbon atoms, 1 to about 3 carbon atoms. Certain embodiments provide that the alkyl is methyl, ethyl, n-propyl, isopropyl, n-butyl, isobutyl, tert-butyl, octyl, decyl, or the like, as well as cycloalkyl groups such as cyclopentyl, cyclohexyl or the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl groups substituted with one or more substituent groups, and include "heteroatom-containing alkyl" and "heteroalkyl," which terms refer to alkyl groups in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl groups, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl groups substituted with one or more substituent groups, and the terms "heteroatom-containing alkenyl" and "heteroalkenyl" refer to alkenyl groups in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl groups, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to an alkynyl group substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include a linear, branched, unsubstituted, substituted, and/or heteroatom-containing alkynyl and lower alkynyl group, respectively.

The term "alkoxy" as used herein intends an alkyl group bound through a single, terminal ether linkage; that is, an "alkoxy" group may be represented as —O—alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aromatic" refers to the ring moieties which satisfy the Hückel 4n+2 rule for aromaticity, and includes both aryl (i.e., carbocyclic) and heteroaryl (also called heteroaromatic) structures, including aryl, aralkyl, alkaryl, heteroaryl, heteroaralkyl, or alk-heteroaryl moieties.

The term "aryl" as used herein, and unless otherwise specified, refers to an aromatic substituent or structure containing a single aromatic ring or multiple aromatic rings that are fused together, directly linked, or indirectly linked (such that the different aromatic rings are bound by a common group such as a methylene or ethylene moiety). Unless otherwise modified, the term "aryl" refers to carbocyclic structures. Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxyphenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctyl-naphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, —O(CO)-aralkyl, wherein "alkyl," "aryl", and "aralkyl" are as defined above.

The terms "cyclic" and "ring" refer to alicyclic or aromatic groups that may or may not be substituted and/or heteroatom-containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic. The term "acyclic" refers to a structure in which the double bond is not contained within a ring structure.

The terms "halo" and "halogen" are used in the conventional sense to refer to a chloro, bromo, fluoro, or iodo substituent.

The term "heteroatom-containing" as in a "heteroatom-containing group" refers to a hydrocarbon molecule or molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted alkyl", "substituted aryl", and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups, such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_1$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl ((CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO—O-alkyl), $C_6$-$C_{24}$ arylcarbonato (—O—(CO)—O-aryl), carboxy (—COOH), carboxylato (—COO—), carbamoyl (—(CO)NH$_2$), mono-($C_1$-$C_{24}$ alkyl)-substituted carbamoyl (—(CO)NH($C_1$-$C_{24}$ alkyl)), di-($C_1$-$C_{24}$ alkyl)-substituted carbamoyl (—(CO)—N(C1-$C_{24}$ alkyl)$_2$), mono-($C_1$-$C_{24}$ haloalkyl)-substituted carbamoyl (—(CO)—NH($C_1$-$C_{24}$ alkyl)), di-($C_1$-$C_{24}$ haloalkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl —($C_5$)—NH$_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)substituted thiocarbamoyl (—(CO)—NH aryl), di-($C_5$-$C_{24}$ aryl)-substituted thiocarbamoyl ((CO)—N($C_5$-$C_{24}$ aryl) z), di-N—($C_1$-$C_{24}$ alkyl), N—($C_5$-$C_{24}$ aryl)-substituted thiocarbamoyl, carbamido (—NH—(CO)—NH2), cyano(—C≡N), cyanato (—O—C≡N), thiocyanato (—S—C≡N), formyl (—(CO)—H), thioformyl (—(CS)—H), amino (—NH$_2$), mono-($C_1$-$C_{24}$ alkyl)-substituted amino, di-($C_1$-$C_{24}$ alkyl)-substituted amino, mono-($C_5$-$C_{24}$ aryl)-substituted amino, di-($C_5$-$C_{24}$ aryl)-substituted amino, $C_1$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (CR=N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$OH), sulfonate (SO$_2$O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl-SO$_2$—N(H) alkyl), $C_1$-$C_{24}$ dialkylaminosulfonyl-SO$_2$—N(alkyl)$_2$, $C_5$-$C_{24}$ arylsulfonyl (—SO$_2$-aryl), boryl (—BH$_2$), borono (B(OH)$_2$), boronato (—B(OR)$_2$ where R is alkyl or aryl), phosphono (—P(O)(OH)$_2$), phosphonato (P(O)(O)$_2$), phosphinato (P(O)(O—)), phospho (—PO$_2$), and phosphine (—PH$_2$); and the moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{24}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

Where substituents are described as "substituted" or "optionally substituted," these Fn substitutions preferably comprise halo, hydroxyl, $C_1$-$C_3$ alkoxy, $C_1$-$C_6$ alkylcarbonyl (CO-alkyl), $C_2$-$C_{24}$ alkoxycarbonyl ((CO)—O-alkyl), carboxy (—COOH), carbamoyl (—(CO)—NH$_2$), mono-($C_1$-$C_6$ alkyl)-substituted carbamoyl (—(CO)NH($C_1$-$C_6$ alkyl)), di-($C_1$-$C_6$ alkyl)-substituted carbamoyl (—(CO)—N($C_1$-$C_6$ alkyl)$_2$), cyano(—C≡N), cyanato (—O—C≡N), thiocyanato (—S—C≡N), formyl (—(CO)—H), amino (—NH$_2$), mono-($C_1$-$C_6$ alkyl)-substituted amino, or di-($C_1$-$C_6$ alkyl) substituted amino.

By "functionalized" as in "functionalized alkyl", "functionalized olefin", "functionalized cyclic olefin", and the like, is meant that in the alkyl, olefin, cyclic olefin, or other moiety, at least one hydrogen atom bound to a carbon (or other) atom is replaced with one or more functional groups such as those described herein and above. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups such as those specifically enumerated above. Analogously, the above-mentioned groups may be further substituted with one or more functional groups such as those specifically enumerated.

In a preferred embodiment of the present invention R is a $C_2$ or $C_3$ alkylene group which is unsubstituted or substituted with one or two, preferably two lower alkyl, preferably methyl or ethyl, more preferably methyl. Preferred examples for R are —CH$_2$—CH$_2$—, —CH$_2$—CH$_2$—CH$_2$—, —CH(CH$_3$)—CH(CH$_3$)— and —CH$_2$—C(CH$_3$)$_2$—CH$_2$—.

In the furfural derivative of Formula (II), $R^2$ independently is H, alkyl, alkenyl or aryl, as defined above. Preferably, $R^2$ independently is H or alkyl, more preferably H or $C_{1-4}$ alkyl, more preferably H or $C_{1-3}$ alkyl, even more preferably H or $C_{1-2}$ alkyl, most preferably H or methyl. In a further preferred embodiment, $R^2$ is H.

In the furfural derivative of Formula (II), $R^5$ is $R^2$, —CH$_2$OR$^2$, —CO$_2$R$^2$ or

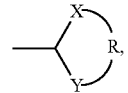

wherein X, Y and R and its preferred embodiments are defined as above.

Preferably, $R^5$ is $R^2$, —CH$_2$OR$^2$ or —CO$_2$R$^2$, wherein $R^2$ is H or alkyl, wherein alkyl preferably is $C_{1-4}$ alkyl, in particular methyl or ethyl.

Certain embodiment of the furfural derivative of Formula (II) are the following compounds:

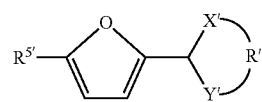

wherein $R^{5'}$ is H, methyl, —CH$_2$OR$^{2'}$, —CO$_2$R$^{2'}$ or

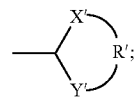

$R^{2'}$ is H or alkyl, preferably H or $C_{1-4}$ alkyl;
X' and Y' are both O or S; and
R' is $C_2$ or $C_3$ alkylene being optionally substituted with one or two $C_{1-4}$ alkyl (preferably methyl);

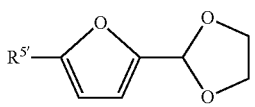

wherein R$^{5'}$ is defined as above;

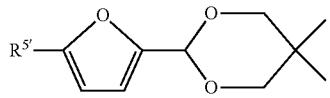

wherein R$^{5'}$ is defined as above;

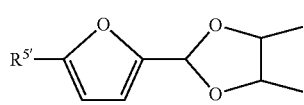

wherein R$^{5'}$ is defined as above; and

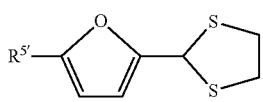

wherein R$^{5'}$ is defined as above.

The furfural derivative of Formula (II) can be obtained for example by reacting furfural with ethylene glycol, substituted ethylene glycol or any other suitable dialcohol. This reaction, which also constitutes a protection of the aldehyde function of the furfural in the form of a cyclic ketal, is known to the person skilled in the art. The protection reaction can, for example, be carried out in a suitable organic solvent, such as cyclohexane, using a suitable catalyst, such as A70 amberlyst resin. For example, a furfural derivative of Formula (II), which is 1,3-dioxolan-2-(2-furanyl) can be obtained quantitatively by reacting furfural with ethylene glycol.

According to the invention it has been found that the furfural derivative of Formula (II) surprisingly reacts with a dienophile resulting in the Diels-Alder adduct of Formula (I) although furfural itself and the dialkyl-ketal derivative of furfural do not form a Diels-Alder adduct with ethylene and its derivatives. The present invention therefore provides a process wherein the furfural derivative of Formula (II) is reacted with the ethylene derivative of Formula (III) thereby resulting in the Diels-Alder condensation adduct of Formula (I).

The ethylene derivative of Formula (III) or (III') bears two substituents, R$^3$ and R$^4$. These substituents independently are H or —CN, provided that at least one of R$^3$ and R$^4$ is —CN. Thus, the ethylene derivative of Formula (III) or (III') bears at least one substituent. In one embodiment, R$^4$ is H and R$^3$ is —CN. Alternatively, R$^3$ and R$^4$ may both be —CN. If both, R$^3$ and R$^4$ are —CN, the ethylene derivative includes the cis- and the trans-isomer of fumaronitrile.

The Diels-Alder condensation reaction between the compound of Formula (II) and the compound of Formula (III) or (III') can be carried out under usual Diels-Alder conditions known to the person skilled in the art. Depending on the specific derivatives employed, the condensation reaction can be carried out in the presence or without any catalysts and also with or without any solvent. The reaction can be carried out at any suitable temperature of from about 10 to about 120° C., preferably from about 20 to about 100° C., more preferably from about 20 to about 80° C., for a time sufficient to convert the starting compounds into the desired Diels-Alder adduct, such as about 2 or 5 seconds to about 6 days, preferably about 3 hours to about 4 days, more preferably about 12 hours to about 4 days, such as about 24 hours. The reaction can be carried out at ambient pressure or increased pressure. Advantageously, the reaction is carried out at ambient pressure, such as about 1000 hPa or at a pressure of up to about 10000 hPa, preferably up to about 5000 hPa, more preferably up to about 2000 hPa.

Advantageously, the Diels-Alder reaction is conducted in the presence of a catalyst, in particular known Diels-Alder catalysts. These catalysts include Lewis acids, e.g. aluminum, boron, zinc, hafnium, or iron compounds, such as AlCl$_3$, Al(Et)Cl$_2$, Al(Et)$_2$Cl, BF$_3$, B(Ac)$_3$, ZnCl$_2$, ZnBr, Zn(Ac)$_2$, ZnI$_2$, CuCl$_2$, Sc(OTf)$_3$, Bi(OTf)$_3$ and BiCl$_3$, FeCl$_3$, Fe(Ac)$_3$, FeCl$_2$ and Fe(Ac)$_2$, Brønsted acids, such a inorganic mineral acids, e.g. sulphuric acid, phosphoric acid, nitric acid, hydrobromic acid or hydrochloric acid, and organic acids, such as methane sulphonic acid, p-toluenesulphonic acid, or carboxylic acids. Diels-Alder catalysts also include halides of tin or titanium, such as SnCl$_4$ and TiCl$_4$. Alternatively, activated carbon, silica, alumina, silica-alumina, zirconia or zeolites may be used. Carbon, silica, alumina, silica-alumina, zirconia and zeolites may be used as such, but they may also be used as support for a catalytically active metal or metal compound. Such metals or metal compounds suitably include alkali metals, alkaline earth metals, transition metals, noble metals, rare earth metals. The catalysts can be acidic, e.g. by treating supports with phosphoric acid, or by ion exchange of zeolites to render them into their acidic form. The catalyst can be an acid catalyst. Examples of solid catalysts include amorphous silica-alumina, zeolites, preferably zeolites in their H-form, and acidic ion exchange resins. Other suitable catalysts that are liquids or that may be dissolved in the appropriate solvent to yield a homogeneous catalyst environment, include organic and inorganic acids, such as alkane carboxylic acid, arene carboxylic acid, sulphuric acid, phosphoric acid, hydrochloric acid, hydrobromic acid and nitric acid.

The Diels-Alder condensation reaction between the compound of Formula (II) and the compound of Formula (III) or (III') results in the oxanorbonene derivative of Formula (I).

Depending on the starting compounds used, the obtained oxanorbonene may be obtained as different isomers. All possible isomers are included within the scope of the present invention.

For example, if the compound of Formula (II) is reacted with acrylonitrile (the compound of Formula (III) wherein one of $R^3$ and $R^4$ is H and the other one is —CN), the resulting oxanorbonene derivative may be an ortho-isomer, a meta-isomer or a mixture of both. In other words, the oxanorbonene derivative can bear the —CN substituent resulting from the compound of Formula (III) either in ortho- or meta-position relative to the protected aldehyde substituent. Furthermore, both the meta-isomer and the ortho-isomer can be present as endo- or exo-isomer. Also these possible isomers are included within the scope of the present invention.

The present inventors found that the various isomers can be distinguished from each other by NMR displacement determination. This is demonstrated in example 1.2 by the four possible isomers obtained as Diels-Alder condensation product between 1,3-dioxolan-2-(2-furanyl) (compound of Formula (II)) and acrylonitrile (compound of Formula (III)).

The various isomers can be present as mixtures of two or more isomers or in the form of single isomers.

It was furthermore surprisingly found that reacting a furfural derivative of Formula (II) wherein X and Y are both O with the compound of Formula (III) or (III') results in about equal amounts of the ortho- and meta-isomers of the oxanorbonene derivative of Formula (I). However, if X and Y in the compound of Formula (II) are both S, then the reaction results in 100% of the ortho-isomer of the oxanorbonene derivative of Formula (I). Thus, by selecting X and Y in the starting compound of Formula (II) the desired oxanorbonene isomer obtained in the Diels-Alder condensation reaction can be selected.

The oxanorbonene derivative of Formula (I) constitutes a valuable intermediate in the preparation of other chemical compounds, such as 2- or 3-cyanobenzaldehyde or 2,3-dicyanobenzaldehyde which in turn can be converted into ortho-xylenediamine, meta-xylenediamine (MXD) or 1,2,3-tri(aminomethyl)benzene according to the following reaction scheme (showing a preferred example of the process according to the present invention):

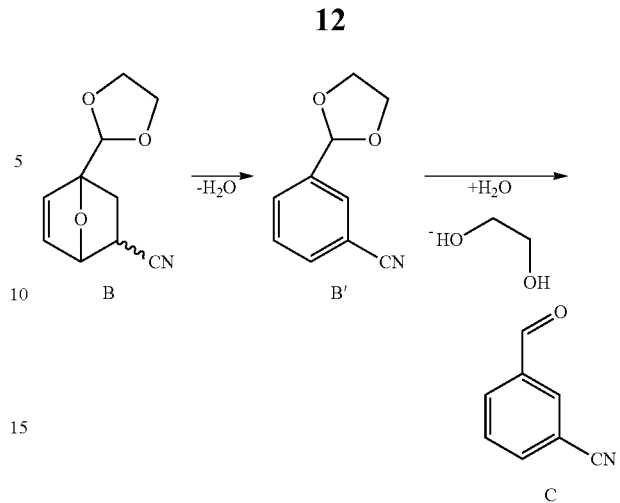

The present invention therefore also relates to a process for the preparation of a compound of Formula (IV)

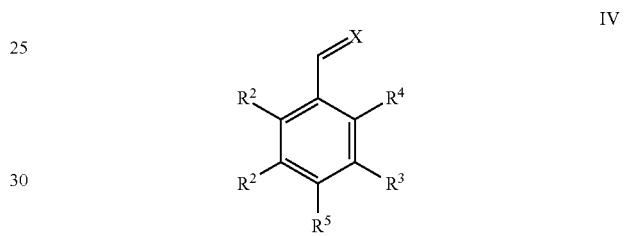

wherein
X is an optionally substituted heteroatom;
$R^2$ is independently H, alkyl, alkenyl or aryl;
$R^3$ and $R^4$ independently are H or —CN, provided that at least one of $R^3$ and $R^4$ is —CN; and
$R^5$ is $R^2$, —$CH_2OR^2$ or —$CO_2R^2$ or

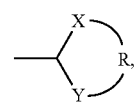

wherein Y is an optionally substituted heteroatom;

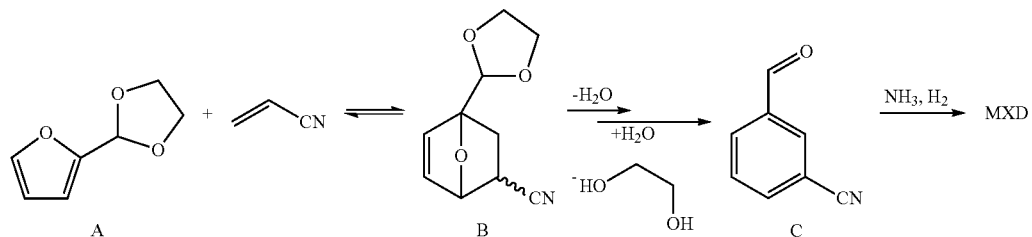

The aromatization and deprotection of the compound of Formula (I) can be carried out in a single step as described above. Alternatively, the desired compound of Formula (IV) can be obtained in a two-step process through the intermediate of the Formula (V). This alternative route is shown in the following reaction scheme which again exemplifies the reaction using preferred compounds:

R is a $C_{1-4}$ alkylene group which may optionally be substituted with one or more $R^1$; and
$R^1$ is a linear or branched, saturated or unsaturated hydrocarbon group which optionally bears one or more functional groups;

a) which comprises dehydration/aromatization of a compound of the Formula (I)

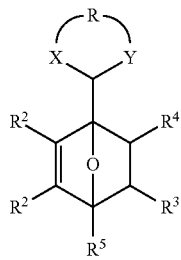

wherein X, Y, R, $R^2$, $R^3$, $R^4$ and $R^5$ are defined as above; to obtain a compound of the Formula (V)

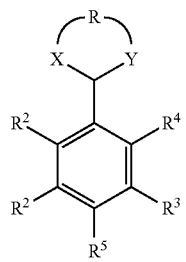

wherein X, Y, R, $R^2$, $R^3$, $R^4$ and $R^5$ are defined as above; followed by deprotection of the compound of Formula (V); or b) which comprises carrying out the dehydration/aromatization and the deprotection of the compound of Formula (I) in a single step.

The reaction conditions for aromatization and deprotection of the compound of Formula (I) are well known to a person skilled in the art. It was, however, surprisingly found that the aromatization reaction of the compound of Formula (I) requires basic reaction conditions, for example in the presence of a methoxide or hydroxide, such as sodium methoxide or sodium hydroxide. For example, the aromatization reaction can be conducted in quantitative yield using sodium methoxide in DMSO at a temperature of 100° C. for about 1 hour. Alcohols, such as methanol and ethanol are other suitable solvents.

Preferably, the compound of Formula (I) is obtained by the above described process using furfural and in particular the cyclic ketal derivative of furfural having the Formula (II) as starting material.

If desired, the compound of Formula (IV) obtained in the above process may be further converted into other chemical compounds, such as for example meta-xylenediamine, ortho-xylenediamine or 1,2,3-tri(aminomethyl)benzene. If meta-xylenediamine is the desired end product, the compound of Formula (IV) preferably is 3-cyanobenzaldehyde, a compound of the Formula (VII')

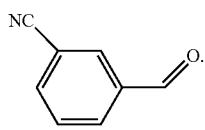

Meta-xylenediamine can be obtained from 3-cyanobenzaldehyde by hydrogenation of the cyano moiety and reductive amination of the aldehyde moiety. Nitrile hydrogenation and reductive amination can be conducted simultaneously, for example by reacting 3-cyanobenzaldehyde in a solution of $NH_3$ in methanol (ratio $NH_3$/3-cyanobenzaldehyde about 19), at 100° C., 50 bar of hydrogen with Co Raney as catalyst. Alternatively, nitrile hydrogenation and reductive amination can be conducted subsequently as shown in the following reaction scheme

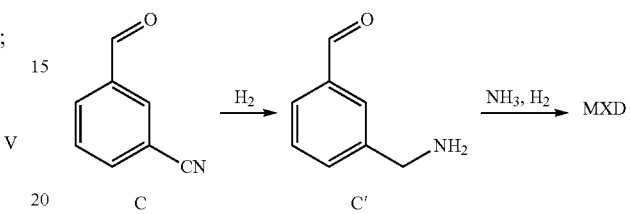

Similarly, ortho-xylenediamine and 1,2,3-tri(aminomethyl)benzene may be obtained.

Thus, the present invention also relates to a process for the preparation of a xylene derivative of the Formula (VI)

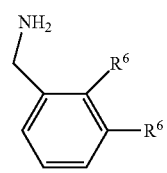

wherein $R^6$ independently is H or —$CH_2$—$NH_2$, provided that at least one of $R^6$ is —$CH_2$—$NH_2$;
which comprises simultaneous or subsequent nitrile hydrogenation and reductive amination of a compound of the Formula (VII)

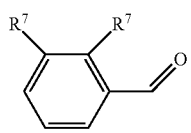

wherein $R^7$ independently is H or —CN, provided that at least one $R^7$ is —CN;
which is obtained by the above described process.

In a further embodiment of the present invention, the process starting from the compounds of Formula (I) and (III) until the compound of Formula (IV) is obtained can be carried out in a single step as one pot reaction.

The compounds of Formula (I) and Formula (V) are novel intermediates useful in the above described processes. Therefore, the present invention also relates to these compounds.

The oxanorbonene derivative of Formula (I) constitutes a valuable intermediate in the preparation of still other chemical compounds.

Indeed, 2- or 3-cyanobenzaldehyde or 2,3-dicyanobenzaldehyde obtained from the oxanorbonene derivative of Formula (I) can also be converted into 2-cyanobenzoic acid, 3-cyanobenzoic acid or 2,3-dicyanobenzoic acid. The conversion of 3-cyanobenzaldehyde (also named m-cyanobenzaldehyde) into 3-cyanobenzoic acid (also named m-cyanobenzoic acid) was described notably in U.S. Pat. No. 6,262,292, the whole content of which is herein incorporated by reference for all purposes. It is exemplified under example 1.6 of present patent title. Using similar reaction conditions, 2-cyanobenzoic acid (o-cyanobenzoic acid) or 2,3-dicyanobenzoic acid can be obtained using respectively 2-cyanobenzaldehyde (also named o-cyanobenzaldehyde) or 2,3-dicyanobenzaldehyde as reagent.

2-cyanobenzoic acid, 3-cyanobenzoic acid or 2,3-dicyanobenzoic acid can in turn be converted into orthophthalic acid, isophthalic acid or hemimellitic acid (also named 1,2,3-benzenetricarboxylic acid). The conversion of 3-cyanobenzoic acid into isophthalic acid can be achieved by adding 3-cyanobenzoic acid to an aqueous solution of a hydroxide (preferably NaOH), then heating at a temperature of at least 50° C. (preferably of at least 100° C.) for at least 10 min (preferably for at least 1 h, more preferably for at least 3 h), then cooling (preferably down to a temperature of at most 50° C., more preferably of at most 30° C.), then acidifying the solution (preferably down to pH=2 or below, more preferably down to pH=1.5 or below) so as to precipitate isophthalic acid. It is exemplified under example 1.7 of present patent title. Using similar reaction conditions, orthophthalic acid or hemimellitic acid can be obtained using respectively o-cyanobenzoic acid or 2,3-dicyanobenzoic acid as reagent.

Alternatively, 2-cyanobenzoic acid, 3-cyanobenzoic acid or 2,3-dicyanobenzoic acid can in turn be converted into 2-aminomethylbenzoic acid, 3-aminomethylbenzoic acid or 2,3-di(aminomethyl)benzoic acid. The conversion of 3-cyanobenzoic acid into 3-aminomethylbenzoic acid was described notably in WO2011/161615 (especially on p. 59), the whole content of which is herein incorporated by reference for all purposes. It is exemplified under example 1.8 of present patent title. Using similar reaction conditions, 2-aminomethylbenzoic acid or 2,3-di(aminomethyl)benzoic acid can be obtained using respectively 2-cyanobenzoic acid or 2,3-dicyanobenzoic acid as reagent.

Should the disclosure of any patents, patent applications, and publications which are incorporated herein by reference conflict with the description of the present patent title to the extent that it may render a term unclear, the present description shall take precedence.

The present invention will now be illustrated by the following examples, which are not intended to be limiting.

EXAMPLE 1

1.1 Furfuryl Dioxolane Synthesis

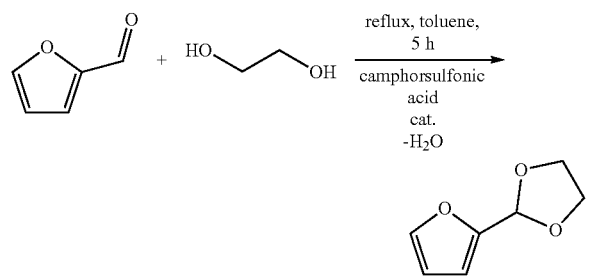

In a two-neck round bottom flask with Dean-Stark trap and magnetic stirring bar, furfural (10.0 g; 103 mmol), toluene (400 ml) and ethylene glycol (4.5 g; 72.5 mmol) were added. Then, camphorsulfonic acid (270 mg; 1.2 mmol) was added to the mixture. The reaction mixture was stirred under reflux during 5 h. The mixture was then cooled to room temperature and was washed with saturated aqueous solution of $NaHCO_3$ (50 ml, 3 times) and then with water (50 ml, 3 times). After drying ($MgSO_4$), the solvent was evaporated and the residue purified by flash chromatography (silica gel, EtOAc/cyclohexane), yielding 8.6 g (85%) of a slight yellow liquid.

1H-NMR (400 Mhz, DMSO):

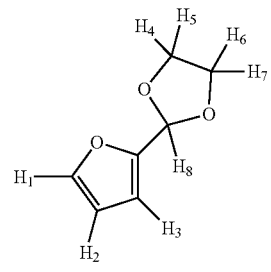

H1: dd: 7.68 ppm
H2: dd: 6.53 ppm
H3: dd: 6.46 ppm
H4, H5, H6, H7: m: 4.03-3.93 ppm
H8: s: 5.89

1.2 Diels-Alder Reaction of 2-(2-furyl)1,3-dioxolane and Acrylonitrile

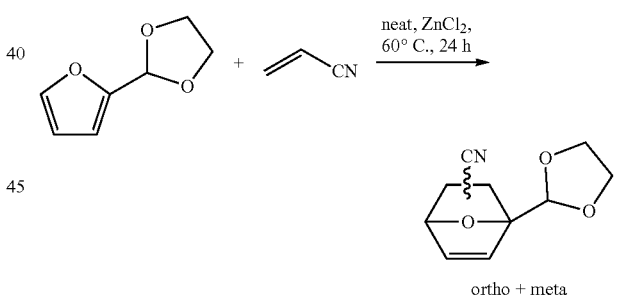

ortho + meta

In a 100 ml single-neck round-bottom flask with condenser and magnetic stirring bar, 2-(2-furyl)1,3-dioxolane (19.80 g; 138.5 mmol) was weighted. Then, acrylonitrile (40.0 g; 746 mmol) and $ZnCl_2$ (2.0 g; 14.4 mmol) were added. The reaction mixture was stirred at 60° C. during 24 h. The conversion is 90% and selectivity in adducts is 93% 1-(1,3-dioxolan-2-yl)-7-oxabicyclo[2.2.1]hept-5-ene-2-carbonitrile and 4-(1,3-dioxolan-2-yl)-7-oxabicyclo[2.2.1]hept-5-ene-2-carbonitrile).

The reaction mixture was concentrated in vacuo to give 27 g of a black thick oil. This crude product was purified by flash chromatography (silica gel, EtOAc/cyclohexane) to afford 11.7 g of expected endo adducts and 7 g of expected exo adducts as slight yellow oils, global isolated yield is 70%. In those conditions repartition of different isomers are ortho/meta 52/48% and endo/exo 66/33%.

1H-NMR (400 Mhz, DMSO):

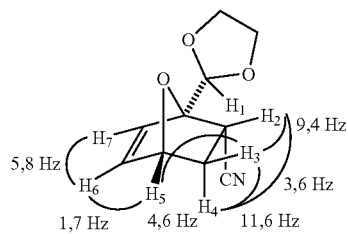

H1: s: 5,28 ppm
H2: dd: 3,11 ppm
H3: ddd: 2,37 ppm
H4: dd: 1,52 ppm
H5: dd: 5,14 ppm
H6: dd: 6,66 ppm
H7: d: 6,46 ppm

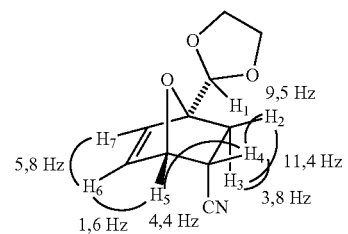

H1: s: 5,23 ppm
H2: dd: 1.41 ppm
H3: dd: 2,20 ppm
H4: m: 3,30 ppm
H5: dd: 5,31 ppm
H6: dd: 6,54 ppm
H7: d: 6,8 ppm

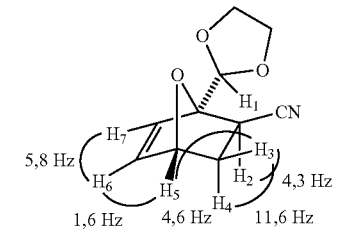

H1: s: 5,32 ppm
H2: qt fortuit: 2,75 ppm
H3: dt: 2,02 ppm
H4: m: 1,88 ppm
H5: dd: 5,18 ppm
H6: dd: 6,52 ppm
H7: d: 6,25 ppm

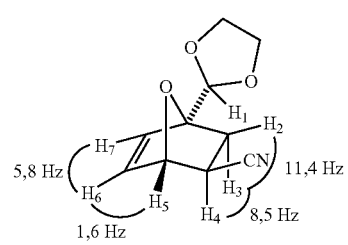

H1: s: 5,27 ppm
H2: m: 1,88 ppm
H3: dd: 1,77 ppm
H4: qt fortuit: 2,75 ppm
H5: d: 5,24 ppm
H6: dd: 6,39 ppm
H7: d: 6,42 ppm

1.3 Conversion of Diels-Alder Adducts of Previous Example to 2-(1,3-dioxolan-2-yl)benzonitrile and 3-(1,3-dioxolan-2-yl)benzonitrile

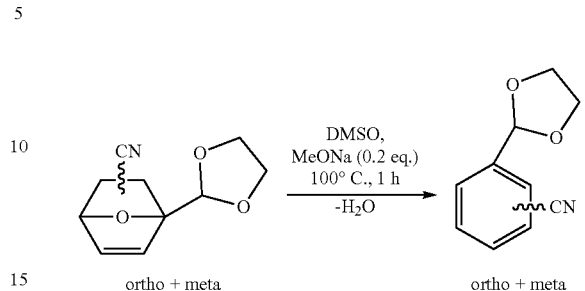

ortho + meta          ortho + meta

In a carousel tube fitted with a PTFE septum screw cap, endo adducts (1.0 g; 5.2 mmol), dimethyl sulfoxide (7.5 ml) and sodium methoxide solution (25 wt. % in methanol; 225 mg; 1.0 mmol) were charged. The reaction mixture was stirred at 100° C. during 1 h. After cooling, the crude product was diluted with dichloromethane (20 ml). The mixture was washed with water (10 ml). The aqueous phase is extracted with dichloromethane (20 ml) and the organic phase was washed with water (10 ml, 3 times). After drying (MgSO4), the solvent was evaporated to afford 840 mg of an oily liquid (93%). A slight hydrolysis of the nitrile group in meta can be observed in those conditions)

1H-NMR (400 Mhz, DMSO):

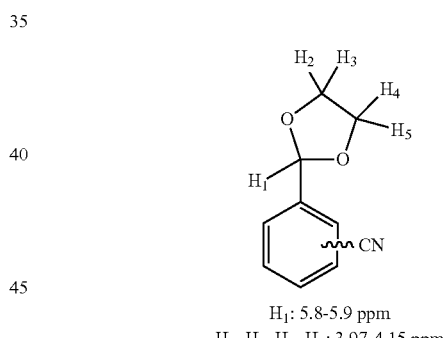

$H_1$: 5.8-5.9 ppm
$H_2$, $H_3$, $H_4$, $H_5$: 3.97-4.15 ppm
H aromatiques: 7.48-7.95 ppm

1.4 Deprotection of 2-(1,3-dioxolan-2-yl)benzonitrile and 3-(1,3-dioxolan-2-yl)benzonitrile to 2-formylbenzonitrile and 3-formylbenzonitrile To a stirred solution of 2- and 3-(1,3-dioxolan-2-yl) benzonitrile (200 mg; 1.14 mmol) in THF (10 ml) was added 1N HCl solution (10 ml) at room temperature. The mixture was heated at 80° C. for 1 h and cooled to room temperature. The reaction mixture was extracted with chloroforme (10 ml, 3 times). The combined chloroforme solution was dried (anhydrous MgSO4), filtered and evaporated under reduced pressure to give 147 mg (98%) of 2-formylbenzonitrile and 3-formylbenzonitrile.

1H-NMR (400 Mhz, DMSO):

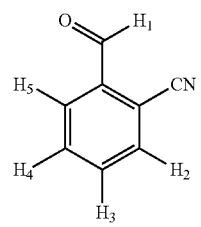

H1: 10.14 ppm
H2, H3, H4, H5: 7.89-8.11 ppm

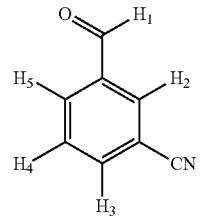

H1: 10.05 ppm
H2, H3, H4, H5: 7.82-8.37 ppm

1.5 Conversion of 3-formylbenzonitrile to 1,3-phenylenedimethanamine

Simultaneous hydrogenation and reductive amination was carried out in batch reactor, containing 113 g of NH3 in MeOH (7 mol/l; d=0.779), 0.7 g of Raney Co and 7 g of 3-formylbenzonitrile, ratio of NH3/aromatic is ~19, at 100° C. and 50 bar of hydrogen during 5 h. Yield was quantitative in metaxylenediamine.

1H-NMR (400 Mhz, DMSO):

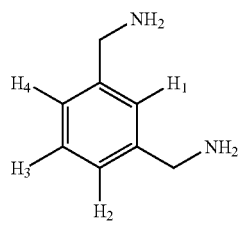

CH2: 3,8 ppm
H1, H2, H3, H4: 7.1-7,4 ppm

1.6 Conversion of m-cyanobenzaldehyde (3-formylbenzonitrile) to m-cyanobenzoic Acid

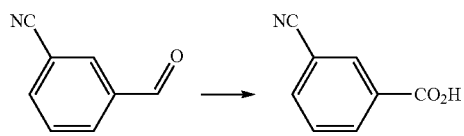 [SMILES: N#Cc1cccc(C=O)c1 ; N#Cc1cccc(C(=O)O)c1]

26.2 g of m-cyanobenzaldehyde, 40 g of dioxane, 17.6 g of sodium hydrogen carbonate, and 100 g of water will be mixed with stirring. 210 g of an aqueous 13.5% by weight sodium hypochlorite solution adjusted to a pH of 9 will be added dropwise over 1 hour while maintaining the internal temperature of the reaction system at 50° C. or less, and the resulting mixture will be stirred for 1 additional hour. Then, 3.6 g of urea will be added and the resulting mixture will be stirred for 20 minutes. Furthermore, 12 g of 98% by weight sulfuric acid and 300 g of water will be added. Precipitated crystals will be formed; they will be filtered, washed with water, and dried to obtain about 27 g (yield: about 92%) of m-cyanobenzoic acid. The purity will be 98% or more.

1.7 Conversion of m-Cyanobenzoic Acid to Isophthalic Acid

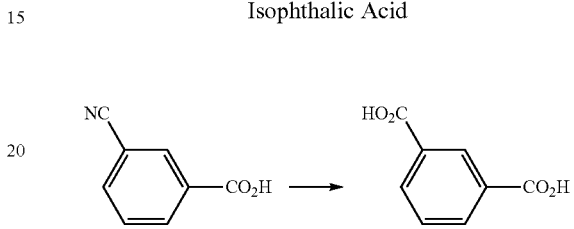

5.0 g of 3-cyanobenzoic acid (m-cyanobenzoic acid) was added to a solution of NaOH (2.93 g) in water (26 g). The resulting solution was heated to reflux (115° C.) for 5 hours. After cooling, 70 ml of water was added and the solution was acidified to pH=1 by dropwise addition of 95% sulfuric acid. A white solid precipitate was formed. The white solid precipitate was filtered and washed 3 times with 10 ml of water. After drying (60° C., 10 mbar, 2 h), 5.44 g of isophthalic acid (96% yield) were obtained.

1.8 Conversion of Isophthalic Acid to 3-Aminomethylbenzoic Acid

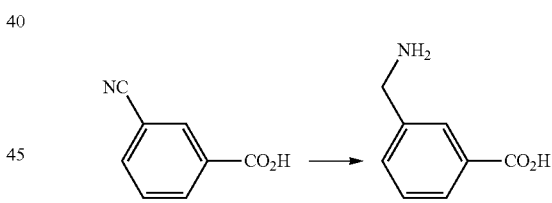

Raney Nickel (0.4 g) will be added at 0° C. to a solution of 3-cyanobenzoic acid (2 g, 13.59 millimoles) in methanol (20 ml), and will be kept under hydrogen atmosphere using $H_2$ balloon at room temperature for 1 hour. After completion, the reaction mixture will be filtered through a prewashed Celite® pad in methanol and will be washed with methanol. The solvent will be evaporated under vacuum to afford the title compound as colorless syrup. About 2 g of 3-aminomethylbenzoic acid will be obtained.

EXAMPLE 2

Similar to example 1.2

The Diels-Alder (DA) condensation with acrylonitrile was conducted using various furfural derivatives thereby determining the different isomers obtained. The results are summarized in the following Table 1.

TABLE 1

| Furfural derivatives | Conditions | Furfural derivative conversion | Global selectivity in DA adducts | Adduct isomers repartition |
|---|---|---|---|---|
| 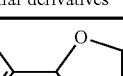 | 0.2 eq. ZnCl2, 24 h, 60° C. | 90% | 93% (rest is retro-DA, not degradation) | Meta: 48% (endo: 30%, exo: 18%) Ortho: 52% (endo: 36%, exo: 15%) |
| 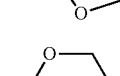 | 0.1 eq. ZnCl2, 24 h, 60° C. | 87% | 95% | Meta: 54% (endo: 30%, exo: 24%) Ortho: 46% (endo: 32%, exo: 14%) |
| 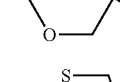 | 0.1 eq. ZnCl2, 24 h, RT | 80% | 100% | Ortho: 100% (endo: 66%, exo: 33%) |
| 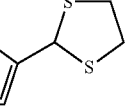 | 0.1 eq. ZnCl2, 24 h, 60° C. | 63% | 93% | ~Meta: 48% (endo: 70%) ~Ortho: 52% (endo: 70%) |

Comparative Example 1

The above example 1 was repeated using 1 eq. of furfural instead of the furfural ethylene glycol ketal. The results are summarized in the following Table 2.

TABLE 2

| Catalyst | Acrylonitrile equivalents | Temperature |
|---|---|---|
| No | 1 | RT, then 60° C. and then 120° C. |
| 10% mol AlCl3 | 1 | RT |
| 30% mol ZnCl2 | 1 | RT then 60° C. |
| No | 0.2 | RT then 60° C. and then 120° C. |
| 10% mol ZnI2 | 0.2 | RT then 60° C. |
| 1 eq. LiCl in EtOH | 1 | 60° C. |
| 10% mol Zn(CN)2 | 1 | RT then 60° C. |

Under none of the conditions summarized in the above table any reaction between furfural and acrylonitrile was observed.

Comparative Example 2

Example 1 was repeated using 1 eq. of the diethyl-ketal of furfural instead of furfural ethylene glycol ketal. The results are summarized in the following Table 3.

TABLE 3

| Catalyst | Acrylonitrile equivalent | Temperature |
|---|---|---|
| No | 1 | RT then 60° C. |
| 10% mol ZnI2 | 1 | RT then 60° C. |

Under none of the reaction conditions summarized in the above Table, any reaction between the diethyl-ketal of furfural and acrylonitrile was observed.

Comparative Example 3

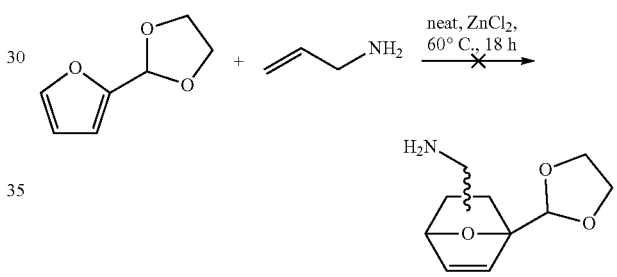

In a carousel tube fitted with a PTFE septum screw cap, 2-(2-furyl)1.3-dioxolane (0.5 g; 3.6 mmol) was weighted. Then, allylamine (1.02 g; 17.9 mmol) and ZnCl2 (195 mg; 0.7 mmol) were added. The reaction mixture was stirred at 60° C. during 18 h. The reaction was monitored by $^1$H NMR spectroscopy.

After stirring at 60° C. for 18 h, no reaction was observed.

The invention claimed is:

1. A process for the preparation of a compound of the Formula (I)

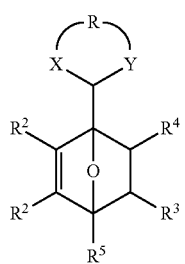

wherein

X and Y are O, or X and Y are S;

R is a $C_{1-4}$ alkylene group which may optionally be substituted with one or more $R^1$;

$R^1$ is a linear, branched and/or cyclic, saturated or unsaturated hydrocarbon alkyl, alkenyl, alkynyl, or aromatic group which optionally bears one or more functional nitro, nitroso, sulfo, sulfonate, cyano, cyanato, thiocyanato, amino, hydroxyl, or carboxyl groups;

$R^2$ independently is H, alkyl, alkenyl or aryl; and $R^3$ and $R^4$ independently are H or —CN, provided that at least one of $R^3$ and $R^4$ is —CN; and $R^5$ is $R^2$, —$CH_2OR^2$, —$CO_2R^2$ or

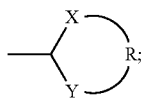

the process comprising reacting a compound of the Formula (II)

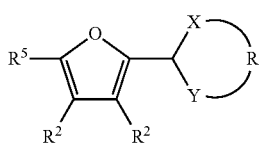

wherein X, Y, R, $R^2$ and $R^5$ are defined as above;
with a compound of the Formula (III) or (III')

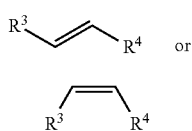

wherein $R^3$ and $R^4$ are defined as above.

2. The process according to claim 1, wherein R is $CH_2$—$CH_2$—, —$CH_2$—$CH_2$—$CH_2$—, —$CH(CH_3)$—$CH(CH_3)$— or —$CH_2$—$C(CH_3)_2$—$CH_2$—.

3. The process according to claim 1, wherein $R^2$ is H.

4. A process for the preparation of a compound of Formula (IV)

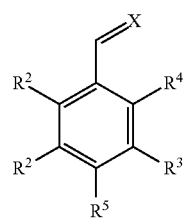

wherein $R^2$ independently is H, alkyl, alkenyl or aryl;

$R^3$ and $R^4$ independently are H or —CN, provided that at least one of $R^3$ and $R^4$ is —CN;

$R^5$ is $R^2$, —$CH_2OR^2$, —$CO_2R^2$ or

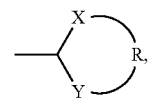

wherein X and Y are O, or X and Y are S;

R is a $C_{1-4}$ alkylene group which may optionally be substituted with one or more $R^1$; and $R^1$ is a linear, branched and/or cyclic, saturated or unsaturated alkyl, alkenyl, alkynyl, or aromatic group which optionally bears one or more nitro, nitroso, sulfo, sulfonate, cyano, cyanato, thiocyanato, amino, hydroxyl, or carboxyl groups;

the process comprising a) dehydration/aromatization of a compound of the Formula (I)

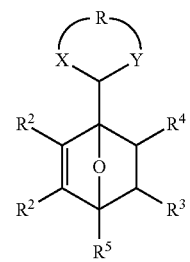

wherein X, Y, R, $R^2$, $R^3$, $R^4$ and $R^5$ are defined as above;
to obtain a compound of the Formula (V)

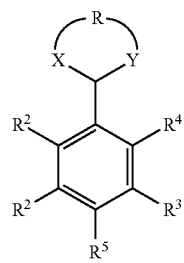

wherein X, Y, R, $R^2$, $R^3$, $R^4$ and $R^5$ are defined as above;
followed by deprotection of the compound of Formula (V);

or comprising b) carrying out the dehydration/aromatization and the deprotection of the compound of Formula (I) in a single step.

5. The process according to claim 4, wherein R is —$CH_2$—$CH_2$—, —$CH_2$—$CH_2$—$CH_2$—, —$CH(CH_3)$—$CH(CH_3)$— or —$CH_2$—$C(CH_3)_2$—$CH_2$—.

6. The process according to claim 4, wherein $R^2$ is H.

7. The process according to claim 4, wherein the compound of Formula (I) is obtained by reacting a compound of the Formula (II)

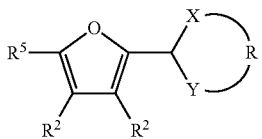

wherein X and Y are O, or X and Y are S;

R is a $C_{1-4}$ alkylene group which may optionally be substituted with one or more $R^1$;

$R^1$ is a linear, branched and/or cyclic, saturated or unsaturated alkyl, alkenyl, alkynyl, or aromatic group which optionally bears one or more nitro, nitroso, sulfo, sulfonate, cyano, cyanato, thiocyanato, amino, hydroxyl, or carboxyl groups;

$R^2$ independently is H, alkyl, alkenyl or aryl; and $R^5$ is $R^2$, —$CH_2OR^2$, —$CO_2R^2$ or

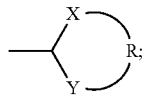

with a compound of the Formula (III) or (III')

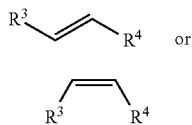

wherein $R^3$ and $R^4$ independently are H or —CN, provided that at least one of $R^3$ and $R^4$ is —CN.

8. A compound of the Formula (I)

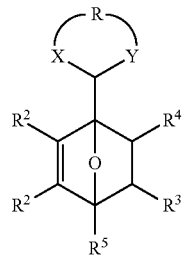

wherein

X and Y are O, or X and Y are S;

R is a $C_{1-4}$ alkylene group which may optionally be substituted with one or more $R^1$;

$R^1$ is a linear, branched and/or cyclic, saturated or unsaturated alkyl, alkenyl, alkynyl, or aromatic group which optionally bears one or more nitro, nitroso, sulfo, sulfonate, cyano, cyanato, thiocyanato, amino, hydroxyl, or carboxyl groups;

$R^2$ independently is H, alkyl, alkenyl or aryl;

$R^3$ and $R^4$ independently are H or —CN, provided that at least one of $R^3$ and $R^4$ is —CN; and $R^5$ is $R^2$, —$CH_2OR^2$, —$CO_2R^2$ or

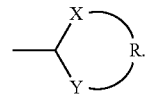

provided that

X and Y are O;

and/or

R is a $C_{1-4}$ alkylene group which is substituted with one or more $R^1$.

9. The compound according to claim 8, wherein R is —$CH_2$—$CH_2$—, —$CH_2$—$CH_2$—$CH_2$—, —$CH(CH_3)$—$CH(CH_3)$— or —$CH_2$—$C(CH_3)_2$—$CH_2$—.

10. The compound according to claim 8, wherein $R^2$ is H.

11. A method comprising obtaining 3- or 2-cyanobenzaldehyde or 2,3-dicyanobenzaldehyde from a compound of Formula (I) made according to the process of claim 1 and converting the 3- or 2-cyanobenzaldehyde or 2,3-dicyanobenzaldehyde into 3-cyanobenzoic acid, 2-cyanobenzoic acid or 2,3-dicyanobenzoic acid, respectively.

12. The method according to claim 11, further comprising converting 3-cyanobenzoic acid, 2-cyanobenzoic acid or 2,3-dicyanobenzoic acid into isophthalic acid, orthophthalic acid or hemimellitic acid.

13. The method according to claim 11, further comprising converting 3-cyanobenzoic acid, 2-cyanobenzoic acid or 2,3-dicyanobenzoic acid into 3-aminomethylbenzoic acid, 2-aminomethylbenzoic acid or 2,3-di(aminomethyl)benzoic acid.

14. The compound according to claim 8, wherein X and Y are O.

15. The compound according to claim 8, wherein R is a $C_{1-4}$ alkylene group which is substituted with one or more $R^1$.

* * * * *